United States Patent
Kane et al.

[11] Patent Number: 5,892,104
[45] Date of Patent: Apr. 6, 1999

[54] CYCLOHEPTENOLS AND THEIR DERIVATIVES, METHODS OF MAKING THEREOF, AND UTILIZATION THEREOF AS FRAGRANCES

[75] Inventors: Bernard J. Kane, Atlantic Beach; Henri M. Hoffmann, Jacksonville, both of Fla.

[73] Assignee: Millenium Specialty Chemicals, Inc., Jacksonville, Fla.

[21] Appl. No.: 799,361

[22] Filed: Feb. 14, 1997

[51] Int. Cl.$^6$ .......................... C07C 69/02; C07C 35/20; A61K 7/46
[52] U.S. Cl. .......................... 560/231; 562/510; 568/671; 568/821; 549/518; 549/543; 549/544; 512/8
[58] Field of Search ...................................... 549/518, 543, 549/544; 568/671, 821; 560/231; 562/510; 512/8

[56] References Cited

U.S. PATENT DOCUMENTS 3,546,279  12/1970  Blumenthal .............................. 260/497

OTHER PUBLICATIONS

Tao, W et al 'Study of cyclized hydration reaction of dimethyl–1,6–octadienes' CA: 127: 293414, 1997.
Hall, JB et al 'Cyclization of dimethyl–1,6–octadienes' CA76: 140005, 1972.
Hall et al., Cyclization of Dimethyl–1,6–octadienes, J. Orgn. Chem, vol. 37, No. 6, 1972, pp. 920–922.

*Primary Examiner*—Amelia Owens
*Attorney, Agent, or Firm*—Needle & Rosenberg, P.C.

[57] ABSTRACT

This invention relates to a compound having the formula I:

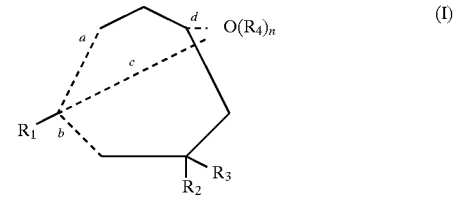

wherein n is an integer of from 0 to 1; when n is 1, one of dashed lines a and b is a single bond and the other of dashed lines a and b is a double bond, dashed line c is not present, and dashed line d is a single bond; when n is 0, dashed lines a, b, c and d are single bonds or one of dashed lines a and b is a single bond and the other of dashed lines a and b is a double bond, dashed line c is not present, and dashed line d is a double bond; $R_1$, $R_2$ and $R_3$ are, independently, lower branched or straight chain alkyl, alkenyl or alkynyl of $C_1$–$C_6$; and $R_4$ is hydrogen, lower branched or straight chain alkyl, alkenyl or alkynyl of $C_1$–$C_5$, or $C(O)R_5$, wherein $R_5$ is hydrogen or lower branched or straight chain alkyl, alkenyl or alkynyl of $C_1$–$C_4$; wherein the sum of the carbon atoms in $R_1$, $R_2$, $R_3$ and $R_4$ is less than or equal to eight carbon atoms. These compounds can be prepared by the cyclization of 1,1,3-trialkyl-1,6-heptadien-3-ols in the presence of an acid. The compounds of formula I are used as fragrance ingredients to confer, enhance, improve, or modify the aroma of a perfumery composition or an article.

41 Claims, No Drawings

CYCLOHEPTENOLS AND THEIR DERIVATIVES, METHODS OF MAKING THEREOF, AND UTILIZATION THEREOF AS FRAGRANCES

BACKGROUND OF THE INVENTION

1. Field of the Invention

This invention relates to cycloheptenols and their derivatives, products therefrom, methods for their use, and methods of synthesis thereof. In particular, the invention provides a convenient synthesis of substituted cycloheptenols and their derivatives and compositions, methods for their use, and articles prepared using the compounds, products and compositions. The compounds are particularly suited for fragrance applications.

2. Background

The use of some organic compounds as fragrance ingredients has been investigated and documented in the literature. In particular, some organic compounds and their derivatives have been used to enhance and improve the aroma of a number of articles, which include fine perfumes, soaps and detergents.

U.S. Pat. No. 3,546,279 discloses the conversion of 5,7-dimethyl-1,6-octadiene to an ester of 3,3,5-trimethyl cycloheptanol by reacting the diene with an acid such as formic acid or acetic acid in the presence of an acid catalyst. This catalyst can be a Lewis acid such as boron trifluoride, aluminum chloride, and stannic chloride, or strong mineral acids like sulfuric or phosphoric acid. Hydrolysis of the ester with water in the presence of an alkali metal hydroxide generated 3,3,5-trimethyl cycloheptanol. Oxidation of the alcohol with aluminum isopropoxide in cyclohexanone, potassium dichromate, or chromic acid produced the ketone.

Using a similar procedure as described above, Hall et al. (*J. Org. Chem.* 1972, 37, 920), disclosed the cyclization of 5,7-dimethyl-1,6-octadiene and 3,7-dimethyl-1,6-octadiene with formic acid in the presence of a Lewis acid catalyst. Hydrolysis of the formate esters to generate the corresponding cycloheptanol followed by oxidation to produce the ketone was also disclosed.

The two references cited above disclose that substituted cycloheptanols and its derivatives, where the seven-member ring is completely saturated, can be used as fragrance ingredients. The present invention describes the synthesis of substituted cycloheptenols and its derivatives, where a unit of unsaturation has been introduced into the ring or, if saturated, it is a bicyclo compound. The starting material 2,4-dimethyl-2,7-octadien-4-ol, which is a by-product made in the pyrolysis of 2-pinanol as disclosed in U.S. Pat. No. 3,240,821 herein incorporated in its entirety by this reference, is available in significant quantity. Until now, no valuable commercial products have been generated from 2,4-dimethyl-2,7-octadien-4-ol. Substituted cycloheptenols and its derivatives are readily available from 2,4-dimethyl-2,7-octadien-4-ol using the present invention. These compounds also possess fragrant aromas, and can be used to confer, enhance, improve, or modify the odor of an article.

Additional advantages of the invention will be set forth in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

SUMMARY OF THE INVENTION

The present invention provides a convenient synthesis of substituted cycloheptenols and their derivatives (i.e., the compounds or compositions formed from performing a specified reaction) and compositions, methods for their use, and articles prepared using the compounds, products, and compositions.

In accordance with the purpose(s) of this invention, as embodied and broadly described herein, this invention, in one aspect, relates to a compound of formula I

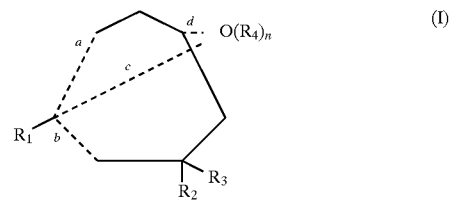

wherein
n is an integer of from 0 to 1;
when n is 1, one of dashed lines a and b is a single bond and the other of dashed lines a and b is a double bond, dashed line c is not present, and dashed line d is a single bond;
when n is 0,
dashed lines a, b, c and d are single bonds, or
one of dashed lines a and b is a single bond and the other of dashed lines a and b is a double bond, dashed line c is not present, and dashed line d is a double bond;
$R_1$, $R_2$ and $R_3$ are, independently, lower branched or straight chain alkyl, alkenyl or alkynyl of $C_1$–$C_6$; and
$R_4$ is hydrogen, lower branched or straight chain allyl, alkenyl or alkynyl of $C_1$–$C_5$ or $C(O)R_5$, wherein $R_5$ is hydrogen or lower branched or straight chain alkyl, alkenyl or alkynyl of $C_1$–$C_4$;
wherein the sum of the carbon atoms in $R_1$, $R_2$, $R_3$ and $R_4$ is less than or equal to eight carbon atoms.

The invention further provides a first method of making the compound of formula I as defined above, wherein
when n is 0, dashed lines a, b, c and d are single bonds;
when n is 1, one of dashed lines a and b is a single bond and the other of dashed lines a and b is a double bond, dashed line c is not present, and dashed line d is a single bond,
$R_1$, $R_2$ and $R_3$ are, independently, lower branched or straight chain alkyl, alkenyl or alkynyl of $C_1$–$C_6$, and $R_4$ is hydrogen or $C(O)H$;
wherein the sum of the carbon atoms in $R_1$, $R_2$, $R_3$ and $R_4$ is less than or equal to eight carbon atoms,
comprising reacting a compound of formula II,

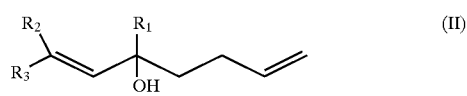

with an acid.

The invention further provides a method of making the compound of formula I, wherein
n is 1, one of dashed lines a and b is a single bond and the other of dashed lines a and b is a double bond, dashed line c is not present, and dashed line d is a single bond;
$R_1$, $R_2$ and $R_3$ are, independently, lower branched or straight chain alkyl, alkenyl or alkynyl of $C_1$–$C_6$; and $R_4$, is lower branched or straight chain alkyl, alkenyl and alkynyl of $C_1$–$C_5$;

wherein the sum of the carbon atoms in $R_1$, $R_2$, $R_3$ and $R_4$ is less than or equal to eight carbon atoms, further comprising reacting the resultant alcohol from the first method with a base and an alkylating agent.

In yet another embodiment, the present invention provides a method of making the compound of formula I, wherein n is 1, one of dashed lines a and b is a single bond and the other of dashed lines a and b is a double bond, dashed line c is not present, and dashed line d is a single bond;

$R_1$, $R_2$ and $R_3$ are, independently, lower branched or straight chain alkyl, alkenyl or alkynyl of $C_1$–$C_6$; and $R_4$ is $C(O)R_5$, wherein $R_5$ is lower branched or straight chain alkyl, alkenyl or alkynyl of $C_1$–$C_4$;

wherein the sum of the carbon atoms in $R_1$, $R_2$, $R_3$ and $R_4$ is less than or equal to eight carbon atoms, further comprising reacting the resultant alcohol from the first method with an alkyl carboxylic acid, alkyl acid anhydride or a mixture thereof.

The invention further provides a method of making the compound of formula I wherein n is 0;

one of dashed lines a and b is a single bond and the other of dashed lines a and b is a double bond, dashed line c is not present, and dashed line d is a double bond; and $R_1$, $R_2$ and $R_3$ are, independently, lower branched or straight chain alkyl, alkenyl or alkynyl of $C_1$–$C_6$;

wherein the sum of the carbon atoms in $R_1$, $R_2$, $R_3$ and $R_4$ is less than or equal to eight carbon atoms, further comprising reacting the resultant alcohol from the first method with an oxidizing agent.

In a further embodiment, the present invention provides a method of using the compound having the formula I to confer, enhance, improve, or modify the aroma of a perfumery composition comprising adding a fragrance effective amount of the compound formula I to a perfumery carrier.

In yet another embodiment, the present invention provides a method of using the compound having the formula I to confer, enhance, improve, or modify the odor properties of an article, comprising adding a fragrance effective amount of the compound to the article.

In yet another aspect, the present invention provides a perfumed composition comprising the compound of formula I.

In addition, the present invention provides a perfumed article comprising an article and a fragrance effective amount of the compound of formula I.

In another embodiment, the invention provides a method for making the compound of formula I, wherein n is 1, one of dashed lines a and b is a single bond and the other of dashed lines a and b is a double bond, dashed line c is not present, and dashed line d is a single bond;

$R_1$, $R_2$ and $R_3$ are, independently, lower branched or straight chain alkyl, alkenyl or alkynyl of $C_1$–$C_6$; and $R_4$ is lower branched or straight chain alkyl, alkenyl and alkynyl of $C_1$–$C_5$;

wherein the sum of the carbon atoms in $R_1$, $R_2$, $R_3$ and $R_4$ is less than or equal to eight carbon atoms, comprising reacting the alcohol of the formula X

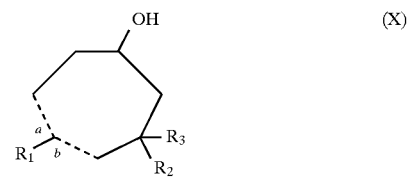

with a base and an alkyating agent.

In yet another embodiment, the invention provides a method for making the compound of formula I, wherein n is 1, one of dashed lines a and b is a single bond and the other of dashed lines a and b is a double bond, dashed line c is not present, and dashed line d is a single bond;

$R_1$, $R_2$ and $R_3$ are, independently, lower branched or straight chain alkyl, alkenyl or alkynyl of $C_1$–$C_6$; and $R_4$ is $C(O)R_5$, wherein $R_5$ is lower branched or straight chain alkyl, alkenyl or alkynyl of $C_1$–$C_4$;

wherein the sum of the carbon atoms in $R_1$, $R_2$, $R_3$ and $R_4$ is less than or equal to eight carbon atoms, comprising reacting the alcohol of formula X with an alkyl carboxylic acid, alkyl acid anhydride or a mixture thereof.

In another embodiment, the invention provides a method for making the compound of formula I, wherein n is 0;

one of dashed lines a and b is a single bond and the other of dashed lines a and b is a double bond, dashed line c is not present, and dashed line d is a double bond; and $R_1$, $R_2$ and $R_3$ are, independently, lower branched or straight chain alkyl, alkenyl or alkynyl of $C_1$–$C_8$;

wherein the sum of the carbon atoms in $R_1$, $R_2$, $R_3$ and $R_4$, is less than or equal to eight carbon atoms, comprising reacting the alcohol of the formula X with an oxidizing agent.

DESCRIPTION OF THE PREFERRED EMBODIMENTS

The present invention may be understood more readily by reference to the following detailed description of preferred embodiments of the invention and the Examples included therein.

Before the present compounds, compositions and methods are disclosed and described, it is to be understood that this invention is not limited to specific synthetic methods, as such may, of course, vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

In this specification and in the claims which follow, reference will be made to a number of terms which shall be defined to have the following meaning:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Preferred alkyl groups herein contain from 1 to 8 carbon atoms.

The term "alkenyl" as used herein refers to a hydrocarbon group of 2 to 24 carbon atoms, with preferred groups within this class containing 2 to 8 carbon atoms, and structural formula containing a carbon-carbon double bond.

The term "alkynyl" as used herein refers to a hydrocarbon group of 2 to 24 carbon atom, with preferred groups within this class containing 2 to 8 carbon atoms, and a structural formula containing a carbon-carbon triple bond.

As used herein, especially in reference to alkyl, alkenyl and alkynyl, the term "lower" refers to a moiety having from 1 to 6 carbon atoms, preferably 1 to 4 or 5 carbon atoms, more preferably 1 to 2 carbon atoms, unless specifically defined to the contrary.

The term "alkylating agent" as provided herein is a compound with the structural formula RX, where R is an alkyl, alkenyl or alkynyl group as previously described, preferably a lower alkylating agent of from one to eight carbon atoms, and X, which is the anion of the alkylating agent, preferably a halide such as chloride, bromide or iodide or a sulfate. It is understood that for the sulfate alkylating agent, multiple alkyl, alkenyl or alkynyl can be used, such as dialkyl sulfate, for example dimethyl sulfate.

The term "alkyl carboxylic acid" as provided herein is a compound which with the structural formula RC(O)OH where R is an alkyl, alkenyl or alkynyl group as described above, preferably less than or equal to seven carbon atoms.

The term "alkyl acid anhydride" as provided herein is a compound with the structural formula [RC(O)]$_2$O, where R is an alkyl, alkenyl or alkynyl group as described above, preferably less than or equal to seven carbon atoms.

The term "oxidizing agent" as used above is a reagent which converts an alcohol of the structural formula RR'CHOH to a compound of the structural formula RR'C=O.

Variables, such as $R_1$, $R_2$, $R_3$, $R_4$, $R_5$, a, b, c, d and n, are understood to have the same meaning throughout, unless stated to the contrary.

In accordance with the purpose(s) of this invention, as embodied and broadly described herein, this invention, in one aspect, relates to a compound of formula I, wherein

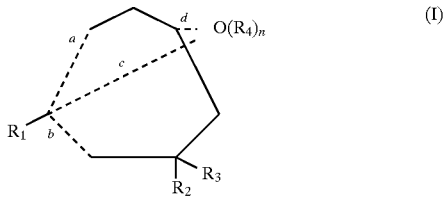

(I)

n is an integer of from 0 to 1;
when n is 1, one of dashed lines a and b is a single bond and the other of dashed lines a and b is a double bond, dashed line c is not present, and dashed line d is a single bond;
when n is 0,
  dashed lines a, b, c and d are single bonds, or
  one of dashed lines a and b is a single bond and the other of dashed lines a and b is a double bond, dashed line c is not present, and dashed line d is a double bond;
$R_1$, $R_2$ and $R_3$ are, independently, lower branched or straight chain alkyl, alkenyl or alkynyl of $C_1$–$C_6$; and $R_4$ is hydrogen, lower branched or straight chain alkyl, alkenyl or alkynyl of $C_1$–$C_5$ or $C(O)R_5$, wherein $R_5$ is hydrogen or lower branched or straight chain alkyl, alkenyl or alkynyl of $C_1$–$C_4$;
wherein the sum of the carbon atoms in $R_1$, $R_2$, $R_3$ and $R_4$ is less than or equal to eight carbon atoms.

When n is 0, the compound is a bicyclo compound or a ketone. When n is 1, the compound is an alcohol, ether or ester, including formate.

When the compound is other than a bicyclo compound, one of a and b is a single bond and the other is a double bond. Thus, both regioisomers are a part of the invention.

$R_1$, $R_2$ and $R_3$ are, independently, and preferably lower branched or straight chain alkyl of $C_1$–$C_6$, more preferably $C_1$–$C_3$, even more preferably methyl or ethyl, even more preferably methyl.

$R_4$ is preferably (i) hydrogen, (ii) lower branched or straight chain alkyl of $C_1$–$C_5$ more preferably $C_1$–$C_3$, even more preferably methyl or ethyl, even more preferably methyl,or (iii) $C(O)R_5$, wherein $R_5$ is preferably hydrogen or lower branched or straight chain alkyl of $C_1$–$C_4$, more preferably hydrogen or $C_1$–$C_3$, even more preferably hydrogen, methyl, or ethyl, even more preferably hydrogen or methyl.

Preferably, the sum of the carbon atoms in $R_1$, $R_2$, $R_3$ and $R_4$ is less than or equal to In one embodiment, $R_1$, $R_2$, and $R_3$ are methyl. In another embodiment, n is 1 and $R_4$ is hydrogen In a further embodiment, n is 1 and $R_4$ is C(O)H. In another embodiment, n is 0 and dashed lines a, b, c and d are single bonds. In yet another embodiment, n is 1 and $R_4$ is $C(O)R_5$, wherein $R_5$ is lower branched or straight chain alkyl, alkenyl or alkynyl of $C_1$–$C_4$. In a further embodiment, n 1 and $R_4$ is lower branched or straight chain alkyl, alkenyl or alkynyl of $C_1$–$C_5$. In another embodiment, n is 0, one of dashed lines a and b is a single bond and the other of dashed lines a and b is a double bond, dashed line c is not present, and dashed line d is a double bond. In one embodiment, the compound is:

a) n is 0, $R_1$, $R_2$ and $R_3$ are methyl, dashed line a is a single bond, dashed line b is a double bond, dashed line c is not present, and dashed line d is a double bond;
b) n is 0, $R_1$, $R_2$ and $R_3$ are methyl, dashed line a is a double bond, dashed line b is a single bond, dashed line c is not present, and dashed line d is a double bond;
c) n is 1, $R_1$, $R_2$ and $R_3$ are methyl, $R_4$ is hydrogen, dashed line a is a single bond, dashed line b is a double bond, dashed line c is not present, and dashed line d is a single bond;
d) n is 1, $R_1$, $R_2$ and $R_3$ are methyl, $R_4$ is hydrogen, dashed line a is a double bond, dashed line b is a single bond, dashed line c is not present, and dashed line d is a single bond;
e) n is 1, $R_1$, $R_2$ and $R_3$ are methyl, $R_4$ is C(O)H, dashed line a is a single bond, dashed line b is a double bond, dashed line c is not present, and dashed line d is a single bond;
f) n is 1, $R_1$, $R_2$ and $R_3$ are methyl, $R_4$ is $C(O)CH_3$ dashed line a is a single bond, dashed line b is a double bond, dashed line c is not present, and dashed line d is a single bond;
g) n is 1, $R_1$, $R_2$ and $R_3$ are methyl, $R_4$ is $C(O)CH_3$, dashed line a is a double bond, dashed line b is a single bond, dashed line c is not present, and dashed line d is a single bond;
h) n is 1, $R_1$, $R_2$, $R_3$ and $R_4$ are methyl, dashed line a is a single bond, dashed line b is a double bond, dashed line c is not present, and dashed line d is a single bond;

i) n is 1, $R_1$, $R_2$, $R_3$ and $R_4$ are methyl, dashed line a is a double bond, dashed line b is a single bond, dashed line c is not present, and dashed line d is a single bond;

j) n is 0, $R_1$, $R_2$ and $R_3$ are methyl, and dashed lines a, b, c and d are single bonds;

k) n is 1, $R_1$, $R_2$ and $R_3$ are methyl, $R_4$ is ethyl, dashed line a is a single bond, dashed line b is a double bond, dashed line c is not present, and dashed line d is a single bond;

l) n is 1, $R_1$, $R_2$ and $R_3$ are ethyl, $R_4$ is hydrogen, dashed line a is a single bond, dashed line b is a double bond, dashed line c is not present, and dashed line d is a single bond;

m) n is 1, $R_1$, $R_2$ and $R_3$ are ethyl, $R_4$ is hydrogen, dashed line a is a double bond, dashed line b is a single bond, dashed line c is not present, and dashed line d is a single bond;

n) n is 1, $R_1$, $R_2$ and $R_3$ are ethyl, $R_4$ is C(O)H, dashed line a is a single bond, dashed line b is a double bond, dashed line c is not present, and dashed line d is a single bond;

o) n is 1, $R_1$, $R_2$ and $R_3$ are ethyl, $R_4$ is C(O)H, dashed line a is a double bond, dashed line b is a single bond, dashed line c is not present, and dashed line d is a single bond;

p) n is 1, $R_1$, $R_2$ and $R_3$ are ethyl, $R_4$ is $C(O)CH_3$, dashed line a is a single bond, dashed line b is a double bond, dashed line c is not present, and dashed line d is a single bond;

q) n is 1, $R_1$, $R_2$ and $R_3$ are ethyl, $R_4$ is $C(O)CH_3$, dashed line a is a double bond, dashed line b is a single bond, dashed line c is not present, and dashed line d is a single bond;

r) n is 1, $R_1$, $R_2$ and $R_3$ are methyl, $R_4$ is butyl, dashed line a is a single bond, dashed line b is a double bond, dashed line c is not present, and dashed line d is a single bond;

s) n is 0, $R_1$, $R_2$ and $R_3$ are ethyl, and dashed lines a, b, c and d are single bonds;

t) n is 0, $R_1$, $R_2$ and $R_3$ are ethyl, dashed line a is a single bond, dashed line b is a double bond, dashed line c is not present, and dashed line d is a double bond; or u) n is 0, $R_1$, $R_2$ and $R_3$ are ethyl, dashed line a is a double bond, dashed line b is a single bond, dashed line c is not present, and dashed line d is a double bond.

Compounds a, c–g, and j are particularly preferred.

The invention further provides a method of making the compound of formula I, wherein when n is 0, dashed lines a, b, c and d are single bonds;

when n is 1, one of dashed lines a and b is a single bond and the other of dashed lines a and b is a double bond, dashed line c is not present, and dashed line d is a single bond;

$R_1$, $R_2$ and $R_3$ are, independently, lower branched or straight chain alkyl, alkenyl or alkynyl of $C_1$–C; and $R_4$ is hydrogen or C(O)H;

wherein the sum of the carbon atoms in $R_1$, $R_2$, $R_3$ and $R_4$ is less than or equal to eight carbon atoms, comprising reacting a compound of formula II,

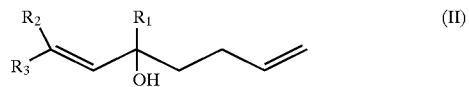

with an acid.

The synthesis of starting compound II is well known to those of skill in the art from, for example, U.S. Pat. No. 3,240,811, particularly at column 2, lines 35–37. Compound II in one embodiment therein is a byproduct of the pyrolysis of 2-pinanol (2,4-dimethyl-2,7-octadien-4-ol ("Isolinalool")). Other variations of Compound II can be prepared using different $R_1$–$R_3$ groups in the same pyrolysis reaction.

In one embodiment, the acid comprises phosphoric acid, sulfuric acid, or formic acid. In another embodiment, $R_1$, $R_2$ and $R_3$ are methyl. In a preferred embodiment, the acid comprises phosphoric or sulfuric acid and (a) n is 1 and $R_4$ is hydrogen or (b) n is 0. In yet another embodiment, the acid is formic acid and n is 1 and $R_4$ is C(O)H.

The addition of compound II to an acid produced the cyclized products III and IV. In the case of compound III, the acid employed is preferably phosphoric acid, sulfuric acid, hydrochloric acid, or nitric acid or mixtures thereof, even more preferably phosphoric acid and sulfuric acid. In the case of compound IV, formic acid was utilized. The acid was stirred with compound II for three hours from –20° C. to 60° C., preferably from 0° C. to 5° C. The concentration of acid added to compound II is dependent on the nature of the acid. When phosphoric acid and sulfuric acid are used, 1.5 to 5.0 moles of acid per mole of compound II was used, while 1.0 to 10.0 moles of formic acid per mole of compound II were used. In addition, hydrolysis of the formate ester IV, generates the alcohol III.

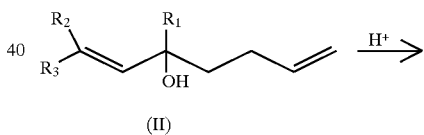

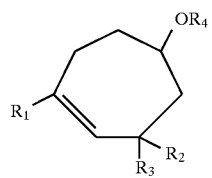

(III): $R_4$ = H
(IV): $R_4$ = COH

The addition of compound II to a solution of phosphoric or sulfuric acid, preferably sulfuric acid, at 0° to 5° C. and held at that temperature for two hours followed by refluxing for seven hours at a pH of about 1.5 to 2.0 resulted in the formation of a mixture comprising compound III, compound V, the regioisomer of compound III, and the bicyclic compound VI. The ratio of V/VI is dependent upon the concentration of the acid and the reaction time. Compound VI can also be prepared in situ from compound II by reacting II with an acid, such as Example 13. In one embodiment, $R_1$, $R_2$ and $R_3$ are, independently, lower branched or straight chain alkyl, alkenyl or alkynyl of $C_1$–$C_6$. In a preferred embodiment, $R_1$–$R_3$ are methyl groups.

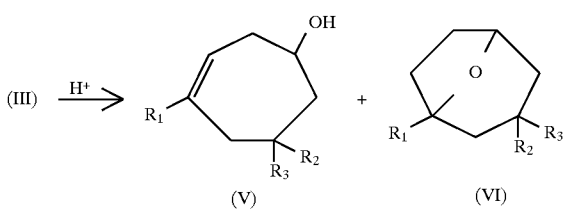

The invention further provides a method of making the compound of formula I, wherein n is 1, one of dashed lines a and b is a single bond and the other of dashed lines a and b is a double bond, dashed line c is not present, and dashed line d is a single bond; $R_1$, $R_2$ and $R_3$ are, independently, lower branched or straight chain alkyl, alkenyl or alkynyl of $C_1$–$C_6$; and $R_4$ is lower branched or straight chain alkyl, alkenyl and alkynyl of $C_1$–$C_5$;

wherein the sum of the carbon atoms in $R_1$, $R_2$, $R_3$ and $R_4$ is less than or equal to eight carbon atoms, further comprising reacting the alcohol, which was produced in the reaction above between formula II and an acid, with a base and an alkylating agent.

In one embodiment, $R_1$, $R_2$ and $R_3$ are methyl and $R_4$ is methyl or ethyl. In another embodiment, the base comprises sodium hydride, sodium hydroxide, potassium hydroxide or silver oxide. In yet another embodiment, the alkylating agent comprises a lower alkyl chloride, bromide, iodide or sulfate.

Compound III can be subjected to further functionalization. In the present invention, compound V, the regioisomer of compound III, can also be functionalized in an identical manner.

The addition of a base and an alkylating agent to a solution compound III in an organic solvent, preferably toluene, generates the ether VII, wherein $R_4$ is lower branched or straight chain alkyl, alkenyl and alkynyl of $C_1$–$C_5$, preferably methyl or ethyl. The base is preferably sodium hydride, sodium hydroxide, potassium hydroxide and silver oxide, even more preferably sodium hydride. The alkyl group of the alkylating agent is preferably lower branched or straight chain alkyl, alkenyl or alkynyl of $C_1$–$C_5$, even more preferably methyl or ethyl. The preferred alkylating agent is methyl iodide or ethyl iodide.

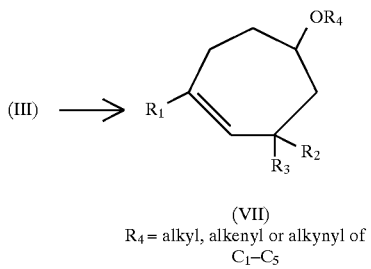

(VII)
$R_4$ = alkyl, alkenyl or alkynyl of $C_1$–$C_5$

In yet another embodiment, the present invention provides a method of making the compound of formula I, wherein n is 1, one of dashed lines a and b is a single bond and the other of dashed lines a and b is a double bond, dashed line c is not present, and dashed line d is a single bond; $R_1$, $R_2$ and $R_3$ are, independently, lower branched or straight chain alkyl, alkenyl or alkynyl of $C_1$–$C_6$; and $R_4$ is C(O)$R_5$ wherein $R_5$ lower branched or straight chain alkyl, alkenyl or alkynyl of $C_1$–$C_4$;

wherein the sum of the carbon atoms in $R_1$, $R_2$, $R_3$ and $R_4$ is less than or equal to eight carbon atoms, further comprising reacting the alcohol produced in the reaction above between formula II and an acid, with an alkyl carboxylic acid, alkyl acid anhydride or a mixture thereof.

In one embodiment, $R_1$, $R_2$, $R_3$ and $R_5$ are methyl. In another embodiment, the alkyl carboxylic acid, alkyl acid anhydride, or a mixture thereof is acetic acid, acetic anhydride or a mixture thereof.

Compound III can be esterified using conventional organic techniques. The addition of an alkyl carboxylic acid, alkyl acid anhydride or mixture thereof to a solution of compound III with or without organic solvent, generates the ester VIII. The addition of a base, preferably dimethylaminopyridine, can increase the rate of the reaction. The alkyl group of the carboxylic acid or acid anhydride is preferably lower branched or straight chain alkyl, alkenyl or alkynyl of $C_1$–$C_4$, even more preferably methyl.

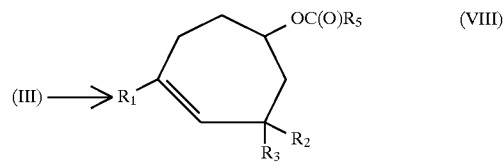

$R_5$ = alkyl, alkenyl or alkynyl $C_1$–$C_4$

The invention further provides a method of making the compound of formula I, wherein n is 0; and one of dashed lines a and b is a single bond and the other of dashed lines a and b is a double bond, dashed line c is not present, and dashed line d is a double bond; and $R_1$, $R_2$ and $R_3$ are, independently, lower branched or straight chain alkyl, alkenyl or alkynyl of $C_1$–$C_6$;

wherein the sum of the carbon atoms in $R_1$, $R_2$, $R_3$ and $R_4$ is less than or equal to eight carbon atoms, further comprising reacting the alcohol produced in the reaction above between formula II and an acid with an oxidizing agent.

In one embodiment, $R_1$, $R_2$ and $R_3$ are methyl. In another embodiment, the oxidizing agent comprises chromium trioxide, copper-zinc oxide in the presence of oxygen, or aluminum alkoxide, such as aluminum isopropoxide, in the presence of cyclohexanone or acetone.

Oxidation of compound III to generate the ketone was readily accomplished by treating compound III with an oxidizing agent to produce compound IX. The oxidizing agent is preferably chromium trioxide, copper-zinc oxide in the presence of oxygen, or aluminum isopropoxide with acetone or cyclohexanone.

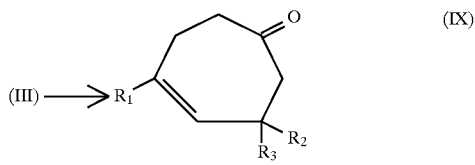

In another embodiment, the invention provides a method for making the compound of formula I, wherein n is 1, one of dashed lines a and b is a single bond and the other of dashed lines a and b is a double bond, dashed line c is not present, and dashed line d is a single bond;

$R_1$, $R_2$ and $R_3$ are, independently, lower branched or straight chain alkyl, alkenyl or alkynyl of $C_1$–$C_6$; and $R_4$ is lower branched or straight chain alkyl, alkenyl and alkynyl of $C_1$–$C_5$;

wherein the sum of the carbon atoms in $R_1$, $R_2$, $R_3$ and $R_4$ is less than or equal to eight carbon atoms, comprising reacting the alcohol of the formula X,

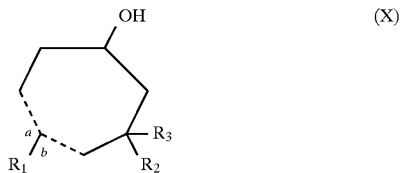 (X)

with a base and an alkylating agent.

The alcohol of formula X is produced by the reaction of formula II with an acid and the alcohol of formula X is preferably isolated.

In yet another embodiment, the invention provides a method for making the compound of formula I, wherein n is 1, one of dashed lines a and b is a single bond and the other of dashed lines a and b is a double bond, dashed line c is not present, and dashed line d is a single bond;

$R_1$, $R_2$ and $R_3$ are, independently, lower branched or straight chain alkyl, alkenyl or alkynyl of $C_1$–$C_6$; and $R_4$ is $C(O)R_5$, wherein $R_5$ is lower branched or straight chain alkyl, alkenyl or alkynyl of $C_1$–$C_4$;

wherein the sum of the carbon atoms in $R_1$, $R_2$, $R_3$ and $R_4$ is less than or equal to eight carbon atoms, comprising reacting the alcohol of formula X with an alkyl carboxylic acid, alkyl acid anhydride or a mixture thereof.

In another embodiment, the invention provides a method for making the compound of formula I, wherein n is 0;

one of dashed lines a and b is a single bond and the other of dashed lines a and b is a double bond, dashed line c is not present, and dashed line d is a double bond;

$R_1$, $R_2$ and $R_3$ are, independently, lower branched or straight chain alkyl, alkenyl or alkynyl of $C_1$–$C_6$;

wherein the sum of the carbon atoms in $R_1$, $R_2$, $R_3$ and $R_4$ is less than or equal to eight carbon atoms, comprising reacting the alcohol of the formula X with an oxidizing agent.

In a further embodiment, the present invention provides a method of using the compound having the formula I to confer, enhance, improve, or modify the aroma of a perfumery composition comprising adding a fragrance effective amount of the compound of formula I to a perfumery carrier. The term "perfumery carrier" as provided herein are solvents and diluents used to prepare the perfumed composition. The perfumery carrier can be any organic solvent or diluent. In one embodiment, the perfumery carrier comprises ethanol, dipropylene glycol, hexylene glycol, benzyl benzoate or diethyl phthalate. The composition can also be used as a fine perfume. In one embodiment, the concentration of the compound of formula I in the composition is from 2% to 50% by weight, preferably 5% to 20% by weight.

In yet another embodiment, the present invention provides a method of using the compound of having the formula I to confer, enhance, improve, or modify the odor properties of an article, comprising adding a fragrance effective amount of the compound to the article.

In yet another aspect, the present invention provides a perfumed composition comprising the compound of formula I. The term "perfumed composition" as provided herein is the mixture of organic compounds which are combined in fixed proportions so that the composition has a pleasant fragrance. In one embodiment, the composition comprises a perfumery carrier. In a preferred embodiment, perfumery carrier comprises ethanol, dipropylene glycol, hexylene glycol, benzyl benzoate or diethyl phthalate. In another embodiment, the concentration of the compound of formula I in the composition is from 2% to 50% by weight. In a further embodiment, the composition is a fine perfume.

The perfume composition itself can be a fine perfume. As outlined in Example 11, the addition of a compound of formula I to a formulation comprising a number of ingredients typically used in the production of a fine perfume can confer, enhance, improve or modify the aroma of the perfume. Other variations of the components added to the compound of Formula I are known to those of skill in the art.

Compound III (n is 1, $R_1$, $R_2$ and $R_3$ are methyl, $R_4$ is hydrogen, dashed line a is a single bond, dashed line b is a double bond, dashed line c is not present, and dashed line d is a single bond) is very diffusive, having a cool, ozony, fruity, character on a fresh woody background. In woody blends, it has a tobacco/tea leaves aroma. Compound IV (n is 1, $R_1$, $R_2$ and $R_3$ are methyl, $R_4$ is C(O)H, dashed line a is a single bond, dashed line b is a double bond, dashed line c is not present, and dashed line d is a single bond) has odor properties similar to Verdyl Acetate, an ingredient common to many fragrance formulations.

Compound VI (n is 0, $R_1$, $R_2$ and $R_3$ are methyl, and dashed lines a, b, c and d are single bonds) has a powerful cineole-like odor. The odor quality of III (n is 1, $R_1$, $R_2$ and $R_3$ are methyl, $R_4$ is hydrogen, dashed line a is a single bond, dashed line b is a double bond, dashed line c is not present, and dashed line d is a single bond)/V (n is 1, $R_1$, $R_2$ and $R_3$ are methyl, $R_4$ is hydrogen, dashed line a is a double bond, dashed line b is a single bond, dashed line c is not present, and dashed line d is a single bond) as a mixture depends upon the amount of each component present. The odor can vary from a fresh, woody, minty, fruity, cooling aroma to a wood cedar amber aroma (see Example 13).

The odor quality of compound VII (n is 1, $R_1$, $R_2$, $R_3$ and $R_4$ are methyl, dashed line a is a single bond, dashed line b is a double bond, dashed line c is not present, and dashed line d is a single bond) was characterized as fresh, spicy, saffron-like, floral (marigold)-herbaceous, woody and powerful. Compound VII (n is 1, $R_1$, $R_2$ and $R_3$ are methyl, $R_4$ is ethyl, dashed line a is a single bond, dashed line b is a double bond, dashed line c is not present, and dashed line d is a single bond) exhibited fresh diffusive citrus lime notes as well as a fruity, peach/prune, rose floral aroma.

The odor quality of VII (n is 1, $R_1$, $R_2$ and $R_3$ are methyl, $R_4$ is $C(O)CH_3$, dashed line a is a single bond, dashed line b is a double bond, dashed line c is not present, and dashed line d is a single bond) is green and fruity-herbaceous with a fresh woody character. When VIII is mixed with the other regioisomer of VIII (n is 1, $R_1$, $R_2$ and $R_3$ are methyl, $R_4$ is $C(O)CH_3$, dashed line a is a double bond, dashed line b is a single bond, dashed line c is not present, and dashed line d is a single bond), the odor varies from a woody, amber, spicy, peppery, fruity aroma to a sharp, woody, fruity camphoraceous aroma depending upon the amount of each regioisomer that is present in the mixture (see Example 14).

Compound IX is characterized as having a powerful, diffusive ocean spray/ozone odor.

In addition, the present invention provides a perfumed article comprising an article and a fragrance effective amount of the compound of formula I.

By the term "fragrance effective amount" of a compound as provided herein is meant a sufficient amount of the compound to provide the desired fragrance. As will be pointed out below, the exact amount required will vary from compound to compound, depending on the desired fragrance. Thus, it is not possible to specify an exact "fragrance effective amount." However, an appropriate effective amount may be determined by one of ordinary skill in the art using only routine experimentation.

The term "article" as provided herein is any item wherein the perfumed compound is added to it in order to confer, enhance, improve, or modify the odor properties of the article. The article can be, but is not limited to, a soap, detergent, fabric softener or air freshener.

The concentrations of the compounds of the present invention can vary depending upon the desired effects as well as the nature of the products to be perfumed. One skilled in the art can vary the concentration of the compounds of the present invention in order to obtain the desired fragrance. The desired fragrance also depends on the nature of the other co-ingredients and solvents in the composition that are typically used by one skilled in the art for preparing perfumery composition. The compounds of the present invention can be directly incorporated into the article to be perfumed, or they can be used as a composition with other perfuming ingredients which is then added to the article to be perfumed. The compounds of the invention are typically used in a range of 0.1% to 20% by weight of the total composition, although more or less can be used depending on the desired results.

EXPERIMENTAL

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and is at room temperature, and pressure is at or near atmospheric.

EXAMPLE 1

Synthesis of 3,3,5-trimethyl-4-cyclohepten-1-ol (n is 1, $R_1$, $R_2$ and $R_3$ are methyl, $R_4$ is hydrogen, dashed line a is a single bond, dashed line b is a double bond, dashed line c is not present, and dashed line d is a single bond).

To a solution of 1,125 gm of 60% of phosphoric acid at 0° to 5° C. was added 375 gm of 2,4-dimethyl-2,7-octadien-4-ol ("Isolinalool") (92% by weight) over 20 min. The mixture was stirred at 0° C. to 5° C. during the addition and for eight hours longer. The mixture was poured into a stirred mixture of 2,300 gm ice and 200 gm hexane. The aqueous layer was separated and the oil phase heated 4 hrs with 600 gm of 15% sodium hydroxide solution to hydrolyse residual phosphate esters. The crude oil was then distilled to produce a total distillate of 178.6 gm, which by GC analysis contained 151 gm of 3,3,5-trimethyl-4-cyclohepten-1-ol. NMR analysis of a purified fraction confirmed its structure.

EXAMPLE 2

Synthesis of 3,3,5-trimethyl-4-cyclohepten-1-ol (n is 1, $R_1$, $R_2$ and $R_3$ are methyl, $R_4$ is hydrogen, dashed line a is a single bond, dashed line b is a double bond, dashed line c is not present, and dashed line d is a single bond)

To a solution of 1,250 gm of 40% sulfuric acid solution at 4° C. was added 500 gm of 2,4dimethyl-2,7-octadien-4-ol (91.2%). The mixture was stirred at 0 to 5° C during the addition and for three hours longer. It was then poured onto 1,200 gm ice and 250 gm of heptane and mixed. The acidic water layer was separated. The oil layer by GC analysis contained 37.6% of 3,3,5-trimethyl-4-cyclohepten-1-ol. It was made basic and distilled to provide 203.8 gm of a fraction that contained 132 gm of the alcohol. Separate work-up of the acidic water layer by neutralization followed by steam distillation provided 136.0 gm of a fraction containing 52% of 4,6,6-trimethyl-3-cyclohepten-1-ol.

EXAMPLE 3

Synthesis of the formate ester of 3,3,5-trimethyl-4-cyclohepten-1-ol (n is 1, $R_1$, $R_2$ and $R_3$ are methyl, $R_4$ is C(O)H, dashed line a is a single bond, dashed line b is a double bond, dashed line c is not present, and dashed line d is a single bond)

2,4-Dimethyl-2,7-octadien-4-ol (92%) 350 gm was added to 875 gm 95% formic acid at 0° C. to 5° C. The mixture was agitated at 0° C. to 5° C. during the one hour addition time and for three hours longer. To the mixture was added 780 gm ice. The reaction mixture was stirred for 30 min. The water layer was separated and the oil washed with dilute base and then with water to provide 353.8 gm of crude oil for distillation. GC analysis indicated the presence of 5.7% of 3,3,5-trimethyl-4-cyclohepten-1-ol and 43.7% of the formate ester. Distillation at reduced pressure gave 198.7 gm of a distillate containing 21.2 gm of the alcohol and 157.8 gm of the formate ester.

EXAMPLE 4

Hydrolysis of the formate ester of 3,3,5-trimethyl-4-cyclohepten-1-ol to generate 3,3,5-trimethyl-4-cyclohepten-1-ol.

Hydrolysis of 175.0 gm of 3,3,5-trimethyl-4-cyclohepten-l1yl formate was accomplished by reflux with 700 gm 14% sodium hydroxide solution for four hours. The crude oil 157 gm contained 88% 3,3,5-trimethyl-4-cyclohepeten-1-ol which was brought to 98% purity by fractional distillation at reduced pressure. The B.P. at 10 mm is 94° C.

EXAMPLE 5

Synthesis of the acetate ester of 3,3,5-trimethyl-4-cyclohepten-1-ol (n is 1, $R_1$, $R_2$ and $R_3$ are methyl, $R_4$is C(O)CH$_3$ dashed line a is a single bond, dashed line b is a double bond, dashed line c is not present, and dashed line d is a single bond)

3,3,5-Trimethyl-4-cyclohepten-1-ol 227 gm, (63%) was refluxed at 124° C. with 300 gm acetic acid, 40 cc heptane and 0.5 gm dimethylaminopyridine under a distillation column capable of separation of the water of esterification. At the end of two days the esterification was 95% complete. Addition of 25 gm acetic anhydride completed the formation of the methyl ester of 3,3,5-trimethyl-4-cyclohepten-1-ol which was distilled at low pressure to give 197 gm of a heart cut having a GC purity of 97–98%.

EXAMPLE 6

Synthesis of 4,6,6-trimethyl-3-cyclohepten-1-ol (n is 1, $R_1$, $R_2$ and $R_3$ are methyl, $R_4$ is hydrogen, dashed line a is a double bond, dashed line b is a single bond, dashed line c is not present, and dashed line d is a single bond) and 1,3,3-trimethyl-8-oxabicyclo[3.21.]octane (n is 0, $R_1$, $R_2$ and $R_3$ and methyl, and dashed lines a, b, and d are single bonds)

3,3,5-Trimethyl-4-cyclohepten-1-ol 50 gm was refluxed 16 hr with 500 gm 5% phosphoric acid and then cohobated from the reaction mixture. The recovered oil weighed 47.6 gm and by GC analysis contained 10% hydrocarbons, 70.6% 1,3,3-trimethyl-8-oxabicyclo[3.2.1]octane and 12% 4,6,6-trimethyl-3-cyclohepten-1-ol. 1,3,3-Trimethyl 8-oxabicyclo [3.2.1]octane has a powerful cineole-like odor.

EXAMPLE 7

Synthesis of the methyl ether of 3,3,5-trimethyl-4-cyclohepten-1-ol (n is 1, $R_1$, $R_2$ and $R_3$ are methyl, $R_4$ is methyl, dashed line a is a single bond, dashed line b is a double bond, dashed line c is not present, and dashed line d is a single bond).

Sodium hydride (60% in mineral oil) (5.4 gm) was added to 60 gm toluene in a stirred reaction flask and stirred under nitrogen. 3,3,5-Trimethyl-4-cyclohepten-1-ol (15.4 gm) was then added over 10 minutes at room temperature and stirred overnight. Iodomethane (21.3 gm) was added dropwise over 10 minutes followed by heating at 45° C. for six hours and four hours at 98° C. The reaction mixture was washed with 50 mL of saturated sodium bicarbonate solution and distilled through a short Vigreux column. A heart cut fraction, 3,3,5-trimethyl-4-cyclohepten-1-yl methyl ether, was obtained that weighed 13.9 gm and had a boiling point of 85° C. at 10 mm pressure. Its GC purity was 97%. The fraction was evaluated for its odor quality and characterized as fresh, spicy, saffron-like, floral, (marigold)-herbaceous-woody-powerful.

EXAMPLE 8

Synthesis of the ethyl ether of 3,3,5-trimethyl-4-cyclohepten-1-ol (n is 1, $R_1$, $R_2$ and $R_3$ are methyl, $R_4$ is ethyl, dashed line a is a single bond, dashed line b is a double bond, dashed line c is not present, and dashed line d is a single bond)

Sodium hydride (60% in mineral oil) (5.4 gm) was added to 60 gm toluene in a reaction flask and stirred under nitrogen. 3,3,5-Trimethyl-4-cyclohepten-1-ol (15.4 gm) was added over 10 minutes at room temperature and stirred for 25 minutes. Iodoethane (23.4 gm) was next added over five minutes. The reaction was heated to 72° C. over 1.5 hours and then four hours at 112° C. The crude oil was washed once with 50 mL saturated sodium bicarbonate solution and distilled through a short Vigreux column. A heart cut fraction, 3,3,5-trimethyl-cyclohepten-1-yl ethyl ether, was obtained that weighed 14.9 gm and had a boiling point of 89° C. at 10 mm pressure. Its GC purity was 94%. The fraction was evaluated for its odor quality and characterized as having fresh diffusive citrus lime notes as well as fruity-peach/prune-rose floral.

EXAMPLE 9

Synthesis of 4,6,6-trimethyl-3-cyclohepten-1-ol (n is 1, $R_1$, $R_2$ and $R_3$ are methyl, $R_4$ is hydrogen, dashed line a is a double bond, dashed line b is a single bond, dashed line c is not present, and dashed line d is a single bond) and 1,3,3-trimethyl-8-oxabicyclo[3.2.1]octane (n is 0, $R_1$, $R_2$ and $R_3$ are methyl, and dashed lines a, b, c and d are single bonds).

To 1,250 gm of 40% sulfuric acid at 0° C. was added 500 gm of 2,4-dimethyl-2,7-octadien-4-ol 88%. The mixture was stirred at 0° C. to 5° C. during 32 minutes of addition and for two hours longer. The mixture was allowed to settle and the lower acid layer 1,189.1 gm (37.1% $H_2SO_4$) was withdrawn. The oil layer, weighing 549.6 gm, was heated at reflux with an equal weight of water. Periodic addition of 20% potassium hydroxide solution was maintained so as to control the pH of the water layer at about 1.5 to 2.0. After less than 7 hours of reflux, the reaction mixture was cooled, neutralized and the oil layer separated. Obtained was 429 gm of oil which had a GC composition of 28% 3,3,5-trimethyl-4-cyclohepten-1-ol, 15% 4,6,6-trimethyl-3-cyclohepten-1-ol and 2% 1,3,3-trimethyl-8-oxobicyclo[3.2.1]octane. Distillation of the oil at reduced pressure provided a fraction weighing 166 gm and which contained 65% 3,3,5-trimethyl-4-cyclohepten-1-ol and 35% 4,6,6-trimethyl-3-cyclohepten-1-ol by GC analysis. The two isomers are not readily separable by fractional distillation.

EXAMPLE 10

Synthesis of the acetate ester of 3,3,5-trimethyl-4-cyclohepten-1-ol (n is 1, $R_1$, $R_2$ and $R_3$ are methyl, $R_4$ is $C(O)CH_3$, dashed line a is a single bond, dashed line b is a double bond, dashed line c is not present, and dashed line d is a single bond)

3,3,5-Trimethyl-4-cyclohepten-1-ol (98%) (50 gm) was added over one hour to refluxing acetic anhydride at 139° C. After one additional hour at reflux, a GC sample showed 100% conversion of the alcohol to the acetate. The reaction was then distilled at reduced pressure (100 mm) through a short Vigreux column to remove acetic acid and excess acetic anhydride. A heart cut fraction of 56 gm was obtained at 10 mm. The boiling point was 95° C. and the GC purity 98%.

EXAMPLE 11

A rose perfume was prepared using 3,3,5-trimethyl-4-cyclohepten-1-ol. The addition of up to 10% gives the formulation a remarkable freshness and naturalness. The formulation was as follows:

|  | wt % |
|---|---|
| Phenyl Ethyl-2-Methylbutyrate 95% | 0.50 |
| Eugenol | 0.50 |
| Phenyl Ethyl Alcohol | 45.00 |
| Guaiacwood Acetate | 0.50 |
| Jasmal | 1.00 |
| Geraniol 95% | 20.00 |
| Rose Crystals | 8.50 |
| Dimethyl Benzyl Carbinyl Acetate | 1.10 |
| Dimethyl Benzyl Carbinyl Butyrate | 0.40 |
| Methyl Dihydro Jasmonate (Hedione) | 1.00 |
| Phenyl Ethyl Phenyl Acetate | 2.00 |
| Phenyl Ethyl Propionate | 1.50 |
| Phenyl Ethyl Isobutyrate | 0.50 |
| Ionone Alpha Refined | 0.50 |
| Citronellol 94% | 7.00 |
| 3,5,5-Triethyl-4-Cyclohepten-1-ol | 10.00 |
|  | 100.00 |

EXAMPLE 12

A fragrance for a soap bar was prepared so as to contain 10% of 3,3,5-trimethyl-4-cyclohepten-1-yl acetate. Its presence provides an interesting green fruity note and brings a remarkable freshness to the soap. The formulation was as follows:

|  | wt % |
|---|---|
| Pinene-Alpha | 1.00 |
| Terpineol | 10.00 |
| Hexanal N | 0.20 |
| Methyl Salicylate | 0.20 |
| Octanal 98% | 0.20 |
| Limonene D Pure | 1.30 |

-continued

| | wt % |
|---|---|
| Camphor D | 0.30 |
| Benzyl Acetate | 3.70 |
| Geranyl Acetate Extra | 5.00 |
| Pheny Ethyl Alcohol | 2.50 |
| Methyl Benzoate | 0.30 |
| Ethyl Butyrate | 0.20 |
| Cyclaprop | 1.60 |
| Isoamyl Salicylate 98% | 1.40 |
| Benzyl Salicylate | 1.50 |
| Gardenol (Styralyl Acetate) | 1.80 |
| Hexyl Cinnamic Aldehyde | 3.50 |
| Vertenex Regular | 20.00 |
| Tetrahydrolinalool | 10.00 |
| Cyclacet | 2.50 |
| Aldehyde $C_{11}$ Undecylenic | 1.10 |
| Geraniol 62% | 2.50 |
| Galaxolide | 3.20 |
| Linalool 96% | 15.50 |
| Menthol L | 0.50 |
| 3,5,5-Trimethyl-4-Cyclohepten-1-yl Acetate | 10.00 |
| | 100.00 |

EXAMPLE 13

Synthesis of 4,6,6trimethyl-3 cyclohepten-1-ol (V) (n is 1, $R_1$, $R_2$ and $R_3$ are methyl, $R_4$ is hydrogen, dashed line a is a double bond, dashed line b is a single bond, dashed line c is not present, and dashed line d is a single bond) and 1,3,3-trimethyl-8-oxabicyclo[3.2.1]octane (VI) (n is 0, $R_1$, $R_2$ and $R_3$ are methyl, and dashed lines a, b, c and d are single bonds).

3,3,5-Trimethyl-4-cyclohepten-1-ol (III) (250 gm) was refluxed with 2500 gm of a 2.5% phosphoric acid solution at 102° C. Samples were removed periodically from the reaction mixture, neutralized and analyzed by gas chromatography. Tabulated below are the results of the isomerization.

| | GC Composition % | | |
|---|---|---|---|
| Hour | VI | V | III |
| 0.0 | — | 0.58 | 98.47 |
| 0.5 | 4.3 | 25.20 | 69.20 |
| 1.0 | 8.2 | 42.20 | 48.30 |
| 2.0 | 15.0 | 57.90 | 24.80 |
| 4.0 | 24.5 | 60.10 | 11.00 |
| 8.0 | 39.7 | 46.70 | 4.80 |

These results show that one can select the reaction time so as to produce the desired action products. Fractional distillation easily separated compound VI from the mixtures alcohols III and V.

Mixtures of alcohol III and V can be used for their fragrance values. For example, such mixtures were evaluated and their odor descriptors were compared to the odor of pure III.

| Sample, Purity % | | |
|---|---|---|
| III | V | Odor Descriptors |
| 99 | — | Diffuse, cool, ozony fruity character on a fresh woody background. |
| 46 | 53 | Fresh, woody, minty, fruity cooling effect - very ozony/see above. |
| 12 | 86 | Wood cedar amber. |

EXAMPLE 14

Syntheses of 3,3,5-trimethyl-4cyclohepten-1-yl acetate (VIII) (n is 1, $R_1$, $R_2$ and $R_3$ are methyl, $R_4$ is $C(O)CH_3$, dashed line a is a single bond, dashed line b is a double bond, dashed line c is not present, and dashed line d is a single bond) and 4,6,6-trimethyl-3-cyclohepten-1-yl acetate (XI) (n is 1, $R_1$, $R_2$ and $R_3$ are methyl $R_4$ is $C(O)CH_3$, dashed line a is a double bond, dashed line b is a single bond, dashed line c is not present, and dashed line d is a single bond).

Two mixtures of alcohols, one having 45% 3,3,5-trimethyl-4-cyclohepten-1-ol (III) and 53% 4,6,6-trimethyl-3-cyclohepten-1-ol (V) and the other having 12% III and 85% V were separately converted to acetate esters using the same conditions as those employed in Example 10. The purified esters were then examined and compared to the odor of pure VIII.

| Sample, Purity % | | |
|---|---|---|
| III VIII | V XI | Odor Descriptors |
| 99 | — | Green, fruity-herbaceous with fresh woody character. |
| 45 | 52 | Woody amber spicy peppery fruity. |
| 10 | 86 | Sharp woody fruity camphoraceous-strong. |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the formula I:

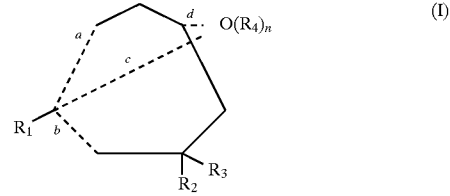

wherein n is an integer of from 0 to 1;
when n is 1, one of dashed lines a and b is a single bond and the other of dashed lines a and b is a double bond, dashed line c is not present, and dashed line d is a single bond;
when n is 0,
dashed lines a, b, c and d are single bonds, or
one of dashed lines a and b is a single bond and the other of dashed lines a and b is a double bond, dashed line c is not present, and dashed line d is a double bond;

$R_1$, $R_2$ and $R_3$ are, independently, lower branched or straight chain alkyl, alkenyl or alkynyl of $C_1$–$C_6$; and $R_4$, is hydrogen, lower branched or straight chain alkyl, alkenyl or alkynyl of $C_1$–$C_5$ or $C(O)R_5$, wherein $R_5$ is hydrogen or lower branched or straight chain alkyl, alkenyl or alkynyl of $C_1$–$C_4$;

wherein the sum of the carbon atoms in $R_1$, $R_2$, $R_3$ and $R_4$ is less than or equal to eight carbon atoms.

2. The compound of claim 1, wherein $R_1$, $R_2$ and $R_3$ are methyl.

3. The compound of claim 2, wherein n is 1 and $R_4$ is hydrogen.

4. The compound of claim 2, wherein n is 0 and dashed lines a, b, c, and d are single bonds.

5. The compound of claim 2, wherein n is 1 and $R_4$ is C(O)H.

6. The compound of claim 2, wherein n is 1 and $R_4$ is $C(O)R_5$, wherein $R_5$ is lower branched or straight chain alkyl, alkenyl or alkynyl of $C_1$–$C_4$.

7. The compound of claim 2, wherein n is 1 and $R_4$ is lower branched or straight chain allyl, alkenyl or alkynyl of $C_1$–$C_5$.

8. The compound of claim 2, wherein n is 0, one of dashed lines a and b is a single bond and the other of dashed lines a and b is a double bond, dashed line c is not present, and dashed line d is a double bond.

9. The compound of claim 1, wherein
a) n is 0, $R_1$, $R_2$ and $R_3$ are methyl, dashed line a is a single bond, dashed line b is a double bond, dashed line c is not present, and dashed line d is a double bond;
b) n is 0, $R_1$, $R_2$ and $R_3$ are methyl, dashed line a is a double bond, dashed line b is a single bond, dashed line c is not present, and dashed line d is a double bond;
c) n is 1, $R_1$, $R_2$ and $R_3$ are methyl, $R_4$ is hydrogen, dashed line a is a single bond, dashed line b is a double bond, dashed line c is not present, and dashed line d is a single bond;
d) n is 1, $R_1$, $R_2$ and $R_3$ are methyl, $R_4$ is hydrogen, dashed line a is a double bond, dashed line b is a single bond, dashed line c is not present, and dashed line d is a single bond;
e) n is 1, $R_1$, $R_2$ and $R_3$ are methyl, $R_4$ is C(O)H, dashed line a is a single bond, dashed line b is a double bond, dashed line c is not present, and dashed line d is a single bond;
f) n is 1, $R_1$, $R_2$ and $R_3$ are methyl, $R_4$ is $C(O)CH_3$, dashed line a is a single bond, dashed line b is a double bond, dashed line c is not present, and dashed line d is a single bond;
g) n is 1, $R_1$, $R_2$ and $R_3$ are methyl, $R_4$ is $C(O)CH_3$, dashed line a is a double bond, dashed line b is a single bond, dashed line c is not present, and dashed line d is a single bond;
h) n is 1, $R_1$, $R_2$, $R_3$ and $R_4$ are methyl, dashed line a is a single bond, dashed line b is a double bond, dashed line c is not present, and dashed line d is a single bond;
i) n is 1, $R_1$, $R_2$ $R_3$ and $R_4$ are methyl, dashed line a is a double bond, dashed line b is a single bond, dashed line c is not present, and dashed line d is a single bond;
j) n is 0, $R_1$, $R_2$ and $R_3$ are methyl, and dashed lines a, b, c and d are single bonds; or
k) n is 1, $R_1$, $R_2$ and $R_3$ are methyl, $R_4$ is ethyl, dashed line a is a single bond, dashed line b is a double bond, dashed line c is not present, and dashed line d is a single bond.

10. A method of making the compound of claim 1 of the formula I, wherein when n is 0, dashed lines a, b, c, and d are single bonds; and when n is 1, $R_4$ is hydrogen or C(O)H;

comprising reacting a compound of formula II,

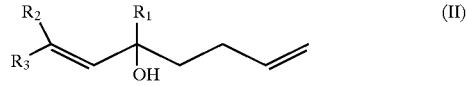

wherein $R_1$, $R_2$, and $R_3$ are as previously defined, with an acid.

11. The method of claim 10, wherein the acid comprises phosphoric acid, sulfur acid, or formic acid.

12. The method of claim 10, wherein $R_1$, $R_2$ and $R_3$ are methyl.

13. The method of claim 10, wherein the acid comprises phosphoric or sulfuric acid and (a) n is 1 and $R_4$ is hydrogen or (b) n is 0.

14. The method of claim 10, wherein the acid is formic acid and n is 1 and $R_4$ is C(O)H.

15. The method of claim 10, further comprising making the compound of the formula I, wherein
n is 1; and
$R_4$ is lower branched or straight chain alkyl, alkenyl and alkynyl of $C_1$–$C_5$;
further comprising reacting the alcohol produced in claim 10 with a base and an alkylating agent.

16. The method of claim 15, wherein $R_1$, $R_2$ and $R_3$ are methyl and $R_4$ is methyl or ethyl.

17. The method of claim 15, wherein the base comprises sodium hydride, sodium hydroxide, potassium hydroxide or silver oxide.

18. The method of claim 15, wherein the alkylating agent comprises a lower alkyl chloride, bromide, iodide or sulfate.

19. The method of claim 10, further comprising making the compound of the formula I, wherein
n is 1; and
$R_4$ is $C(O)R_5$, wherein $R_5$ is lower branched or straight chain alkyl, alkenyl or alkynyl of $C_1$–$C_4$;
further comprising reacting the alcohol produced in claim 10 with an alkyl carboxylic acid, alkyl acid anhydride or a mixture thereof.

20. The method of claim 19, wherein the alkyl carboxylic acid, alkyl acid anhydride, or a mixture thereof is acetic acid, acetic anhydride or a mixture thereof.

21. The method of claim 19, wherein $R_1$, $R_2$, $R_3$, and $R_5$ are methyl.

22. The method of claim 10, further comprising making the compound of the formula I, wherein
n is 0; and
one of dashed lines a and b is a single bond and the other of dashed lines a and b is a double bond, dashed line c is not present, and dashed line d is a double bond;
further comprising reacting the alcohol produced in claim 10 with an oxidizing agent.

23. The method of claim 22, wherein the oxidizing agent comprises (a) chromium trioxide, (b) copper-zinc oxide in the presence of oxygen, or (c) aluminum alkoxide in cyclohexanone or acetone.

24. The method of claim 22, wherein $R_1$, $R_2$ and $R_3$ are methyl.

25. A method of using the compound of claim 1 to confer, enhance, improve, or modify the aroma of a perfumery composition comprising adding a fragrance effective amount of the compound of formula I to a perfumery carrier.

26. The method of claim 25, wherein the concentration of the compound of formula I in the composition is from 2% to 50% by weight.

27. The method of claim 25, wherein the perfumery carrier comprises ethanol, dipropylene glycol, hexylene glycol, benzyl benzoate or diethyl phthalate.

28. The method of claim 25, wherein the composition is a fine perfume.

29. A method of using the compound of claim 1 to confer, enhance, improve, or modify the odor properties of an article, comprising adding a fragrance effective amount of the compound of claim 1 to the article.

30. The method of claim 29, wherein the article is a soap, detergent, fabric softener, or air freshener.

31. A perfumed composition comprising the compound of claim 1.

32. The composition of claim 31, further comprising a perfumery carrier.

33. The composition of claim 32, wherein the concentration of the compound of formula I in the composition is from 2% to 50% by weight.

34. The composition of claim 32, wherein the perfumery carrier comprises ethanol, dipropylene glycol, hexylene glycol, benzyl benzoate or diethyl phthalate.

35. The composition of claim 32, wherein the composition is a fine perfume.

36. A perfumed article comprising an article and a fragrance effective amount of the compound of claim 1.

37. The article of claim 36, wherein the article is a soap, detergent, fabric softener or air freshener.

38. A method for making the compound of claim 1 of the formula I, wherein n is 1; and $R_4$ is lower branched or straight chain alkyl, alkenyl and alkynyl of $C_1$–$C_5$;

comprising reacting the alcohol of the formula X

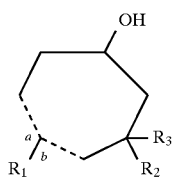

with a base and an alkylating agent.

39. A method for making the compound of claim 1 of the formula I, wherein n is 1; and $R_4$ is $C(O)R_5$, wherein $R_5$ is lower branched or straight chain alkyl, alkenyl or alkynyl of $C_1$–$C_4$;

comprising reacting the alcohol of formula X

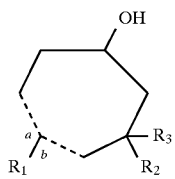

with an alkyl carboxylic acid, alkyl acid anhydride or a mixture thereof.

40. A method for making the compound of claim 1 of the formula I, wherein n is 0; and one of dashed lines a and b is a single bond and the other of dashed lines a and b is a double bond, dashed line c is not present, and dashed line d is a double bond;

comprising reacting the alcohol of the formula X

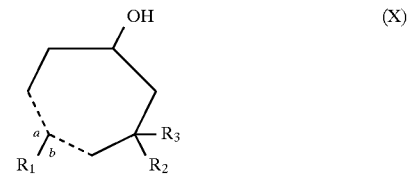

with an oxidizing agent.

41. The compound of claim 1, wherein a) n is 0, $R_1$, $R_2$ and $R_3$ are methyl, dashed line a is a single bond, dashed line b is a double bond, dashed line c is not present, and dashed line d is a double bond;

b) n is 1, $R_1$, $R_2$ and $R_3$ are methyl, $R_4$ is hydrogen, dashed line a is a single bond, dashed line b is a double bond, dashed line c is not present, and dashed line d is a single bond;

c) n is 1, $R_1$, $R_2$ and $R_3$ are methyl, $R_4$ is hydrogen, dashed line a is a double bond, dashed line b is a single bond, dashed line c is not present, and dashed line d is a single bond;

d) n is 1, $R_1$, $R_2$ and $R_3$ are methyl, $R_4$ is C(O)H, dashed line a is a single bond, dashed line b is a double bond, dashed line c is not present, and dashed line d is a single bond;

e) n is 1, $R_1$, $R_2$ and $R_3$ are methyl, $R_4$ is $C(O)CH_3$, dashed line a is a single bond, dashed line b is a double bond, dashed line c is not present, and dashed line d is a single bond;

f) n is 1, $R_1$, $R_2$ and $R_3$ are methyl, $R_4$ is $C(O)CH_3$, dashed line a is a double bond, dashed line b is a single bond, dashed line c is not present, and dashed line d is a single bond; or g) n is 0, $R_1$, $R_2$ and $R_3$ are methyl, and dashed lines a, b, c and d are single bonds.

* * * * *